US010022337B2

(12) United States Patent
Teleki et al.

(10) Patent No.: US 10,022,337 B2
(45) Date of Patent: Jul. 17, 2018

(54) FORMULATION OF SPARINGLY SOLUBLE COMPOUNDS BY HOT-MELT EXTRUSION

(71) Applicant: DSM IP ASSETS B.V., Heerlen (NL)

(72) Inventors: Alexandra Teleki, Kaiseraugst (CH); Camille Adler, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/034,242

(22) PCT Filed: Nov. 14, 2014

(86) PCT No.: PCT/EP2014/074565
§ 371 (c)(1),
(2) Date: May 4, 2016

(87) PCT Pub. No.: WO2015/071394
PCT Pub. Date: May 21, 2015

(65) Prior Publication Data
US 2016/0271077 A1 Sep. 22, 2016

(30) Foreign Application Priority Data

Nov. 15, 2013 (EP) .................................. 13193116

(51) Int. Cl.
| *A61K 31/015* | (2006.01) |
| *A23P 30/20* | (2016.01) |
| *A23K 40/25* | (2016.01) |
| *A61K 9/14* | (2006.01) |
| *A23K 20/179* | (2016.01) |
| *A23L 1/00* | (2006.01) |
| *A23L 1/275* | (2006.01) |

(52) U.S. Cl.
CPC .......... *A61K 31/015* (2013.01); *A23K 20/179* (2016.05); *A23K 40/25* (2016.05); *A23L 1/0076* (2013.01); *A23L 1/275* (2013.01); *A23P 30/20* (2016.08); *A61K 9/146* (2013.01); *A23V 2002/00* (2013.01)

(58) Field of Classification Search
CPC ...... A61K 31/015; A61K 9/146; A23K 20/25; A23P 30/20
See application file for complete search history.

(56) References Cited

U.S. PATENT DOCUMENTS

| 5,939,099 A | 8/1999 | Grabowski et al. |
| 5,972,395 A | 10/1999 | Saleeb et al. |
| 2010/0047340 A1 | 2/2010 | McGinity et al. |

FOREIGN PATENT DOCUMENTS

| DE | 195 36 387 | 4/1997 |
| WO | WO 2008/080037 | 7/2008 |

OTHER PUBLICATIONS

International Search Report for PCT/EP2014/074565, dated Dec. 23, 2014, 3 pages.
Database WPI, Week 201266, 2012, Thomson Scientific—CN 102451 179, May 16, 2012.

*Primary Examiner* — Samantha L Shterengarts
(74) *Attorney, Agent, or Firm* — Nixon & Vanderhye P.C.

(57) ABSTRACT

The present invention relates to formulation of sparingly-(water)-soluble compounds and its use as (or in a) food or feed product or dietary supplement.

13 Claims, No Drawings

FORMULATION OF SPARINGLY SOLUBLE COMPOUNDS BY HOT-MELT EXTRUSION

This application is the U.S. national phase of International Application No. PCT/EP2014/074565 filed 14 Nov. 2014, which designated the U.S. and claims priority to EP Patent Application No. 13193116.4 filed 15 Nov. 2013, the entire contents of each of which are hereby incorporated by reference.

The present invention relates to formulation of sparingly-(water)-soluble compounds and its use as (or in a) food or feed product or dietary supplement.

Hot-melt extrusion as a method of preparing pharmaceutical formulations has previously been disclosed.

Many researchers have utilized hot-melt extrusion techniques to produce pharmaceutical preparations in various forms.

Due to the importance of such formulations there is always a need for new and improved formulations, also in the field of food, feed and dietary supplements.

Therefore the present invention relates to a hot-melt extruded formulation (HEF) comprising
 (i) 0.5-50 weight-% (wt-%), preferably 5-20 wt-%, more preferably 5-10 wt-%, based on the total weight of the hot-melt extruded formulation, of at least one compound having low permeability and low solubility, and
 (ii) 50-99.5 wt-%, preferably 80-95 wt-%, more preferably 90-95 wt-%, based on the total weight of the hot-melt extruded formulation, of at least one polymeric carrier material.

In all the described and disclosed hot-melt extruded formulation the wt-%'s always add up to 100%.

Such a hot-melt extruded formulation has (for example) the following advantages:
 (i) compound having low permeability and low solubility (especially in water) is made bioavailable by this formulation; and
 (ii) such a formulation is stable in food and feed products and dietary supplements; and
 (iii) the process of production is carried out in a continuous manner; and
 (iv) the process of production is carried without any solvents; and
 (v) such a formulation is not known for carotenoids.

The term "compound having low solubility" is to be understood in analogy of the Biopharmaceutical Classification System (BCS) as a compound of Class IV. The BCS is related to drugs, but we like also to include compounds which have the same properties and which are not defined as drugs such as especially carotenoids.

In the following the BCS is further explained.
The Biopharmaceutical Classification System is a system to differentiate the drugs on the basis of their solubility and permeability.

This system restricts the prediction using the parameters solubility and intestinal permeability. The solubility classification is based on a United States Pharmacopoeia (USP) aperture. The intestinal permeability classification is based on a comparison to the intravenous injection. All those factors are highly important because 85% of the most sold drugs in the United States and Europe are orally administered.

There are four classes (Class I-IV) in the BCS.
According to the BCS, drug substances are classified as follows:
Class I—high permeability, high solubility
Class II—high permeability, low solubility
Class III—low permeability, high solubility
Class IV—low permeability, low solubility
Example: hydrochlorothiazide
The drugs are classified in BCS on the basis of following parameters:
1. Solubility
2. Permeability
3. Dissolution This classification system is well known in the prior art and used widely.

Preferred compounds, which have low permeability and low solubility according to the BCS, are carotenoids.

Therefore the present invention also relates to a hot-melt extruded formulation (HEF$^1$), which is (HEF), wherein the compounds, which have low solubility are carotenoids.

There are over 600 known carotenoids; they are split into two classes, xanthophylls (which contain oxygen) and carotenes (which are purely hydrocarbons, and contain no oxygen). All carotenoids are tetraterpenoids, meaning that they are produced from 8 isoprene molecules and contain 40 carbon atoms.

The term "carotenoid" as used herein comprises a natural or synthetic carotene or structurally related polyene compound which can be used as a functional health ingredient or colorant for food, such as α- or β-carotene, 8'-apo-β-carotenal, 8'-apo-β-carotenoic acid esters such as the ethyl ester, canthaxanthin, astaxanthin, lycopene, lutein, zeaxanthin or crocetin, or mixtures thereof. The preferred carotenoid is β-carotene, 8'-apo-β-carotenal, lycopene and lutein and mixtures thereof, especially β-carotene.

Therefore a preferred embodiment of the present invention relates to hot-melt extruded formulation as described above, wherein the compound having low permeability and low solubility is chosen from the groups of carotenoids consisting of α-carotene, β-carotene, 8'-apo-β-carotenal, 8'-apo-β-carotenoic acid esters such as the ethyl ester, canthaxanthin, astaxanthin, lycopene, lutein, zeaxanthin and crocetin, preferably β-carotene.

Therefore the present invention also relates to a hot-melt extruded formulation (HEF$^2$), which is (HEF) or (HEF$^1$), wherein the compound having low permeability and low solubility is chosen from the groups of carotenoids consisting of α-carotene, β-carotene, 8'-apo-β-carotenal, 8'-apo-β-carotenoic acid esters such as the ethyl ester, canthaxanthin, astaxanthin, lycopene, lutein, zeaxanthin and crocetin, preferably β-carotene.

Therefore the present invention also relates to a hot-melt extruded formulation (HEF$^3$), which is (HEF) or (HEF$^1$), wherein the compound having low permeability and low solubility is β-carotene.

The compound having low permeability and low solubility (especially the carotenoids as defined above) is in an amorphous form after the hot-melt extrusion processing.

Therefore the present invention also relates to a hot-melt extruded formulation (HEF$^4$), which is (HEF), (HEF$^1$), (HEF$^2$) or (HEF$^3$), wherein the compound having low solubility is in an amorphous form after the hot-melt extrusion processing.

The hot-melt extruded formulation comprises a polymeric carrier material. This carrier material can be natural as well as synthetic.

Suitable polymeric carrier material are polyethylene oxide; polyvinylpyrrolidon polypropylene oxide; polyvinylpyrrolidone-co-vinylacetate; acrylate and methacrylate copolymers; polyethylene; polycaprolactone; polyethylene-co-polypropylene; alkylcelluloses such as methylcellulose; hydroxyalkylcelluloses such as hydroxymethylcellulose, hydroxyethylcellulose, hydroxypropylcellulose, and hydroxybutylcellulose; hydroxyalkyl alkylcelluloses such as hydroxyethyl methylcellulose and hydroxypropyl methylcellulose; starches, pectins; polysaccharides such as tragacanth, gum arabic, guar gum, sucrose sterate, xanthan gum, lipids, waxes, mono, di, and tri glycerides, cetyl alcohol, steryl alcohol, parafilm waxes and the like, hydrogenated vegetable and castor oil, glycerol monostearte, polyolefins including xylitol, manitol, and sorbitol, alpha hydroxyl acids including citric and tartaric acid edipic acid meleaic acid malic acid, citric acid, enteric polymers such as CAP, HPMC AS, shellac, and a combination thereof.

Therefore the present invention also relates to a hot-melt extruded formulation (HEF$^5$), which is (HEF), (HEF$^1$), (HEF$^2$), (HEF$^3$) or (HEF$^4$), wherein polymeric carrier material is chosen from the group consisting of polyethylene oxide; polyvinylpyrrolidon polypropylene oxide; polyvinylpyrrolidone-co-vinylacetate; acrylate and methacrylate copolymers; polyethylene; polycaprolactone; polyethylene-co-polypropylene; alkylcelluloses such as methylcellulose; hydroxyalkylcelluloses such as hydroxymethylcellulose, hydroxyethylcellulose, hydroxypropylcellulose, and hydroxybutylcellulose; hydroxyalkyl alkylcelluloses such as hydroxyethyl methylcellulose and hydroxypropyl methylcellulose; starches, pectins; polysaccharides such as tragacanth, gum arabic, guar gum, sucrose sterate, xanthan gum, lipids, waxes, mono, di, and tri glycerides, cetyl alcohol, steryl alcohol, parafilm waxes and the like, hydrogenated vegetable and castor oil, glycerol monostearte, polyolefins including xylitol, manitol, and sorbitol, alpha hydroxyl acids including citric and tartaric acid edipic acid meleaic acid malic acid, citric acid, enteric polymers such as CAP, HPMC AS, shellac, and a combination thereof.

Preferred polymeric carrier material in the context of the present invention are cellulose based polymers like ethyl cellulose (EC), hydroxypropylmethyl cellulose (HPMC), or alginate, chitosan, corn or potatoe starch are examples of the natural polymers. Polyvinylpyrrolidon (PVP), polyvinylacetate (PVA), polylactic acid (PLA) or copolymer like poly (methacrylic acid-co-ethyl acrylate) (Eudragit® from Evonik Industries) and polyvinyl caprolactam-polyvinyl acetate-polyethylene glycol graft copolymer (Soluplus® from BASF) are commonly used as synthetic polymers.

Therefore the present invention also relates to a hot-melt extruded formulation (HEF$^6$), which is (HEF), (HEF$^1$), (HEF$^2$), (HEF$^3$), (HEF$^4$) or (HEF$^5$), wherein the polymeric carrier material is chosen from the group consisting of cellulose based polymers like ethyl cellulose (EC), hydroxypropylmethyl cellulose (HPMC), or alginate, chitosan, corn or potato starch are examples of the natural polymers; polyvinylpyrrolidon (PVP), polyvinylacetate (PVA), polylactic acid (PLA) or copolymer like poly(methacrylic acid-co-ethyl acrylate) (Eudragit® from Evonik Industries) and polyvinyl caprolactam-polyvinyl acetate-polyethylene glycol graft copolymer (Soluplus® from BASF).

All these carrier material are commercially available.

Furthermore the hot-melt extruded formulation can optionally comprise at least one plasticizer.

Therefore the present invention also relates to a hot-melt extruded formulation (HEF$^7$), which is (HEF), (HEF$^1$), (HEF$^2$), (HEF$^3$), (HEF$^4$), (HEF$^5$) or (HEF$^6$), wherein the hot-melt extruded formulation additionally comprises at least one plasticizer.

As used herein, the term "plasticizer" includes all compounds capable of plasticizing the polymeric carrier of the invention.

Plasticizers also generally reduce the viscosity of a polymer melt thereby allowing for lower processing temperature and extruder torque during hot-melt extrusion.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly (ethylene glycol), citrate ester-type plasticizers, triacetin, propylene glycol and glycerin.

Such plasticizers can also be ethylene glycol, 1,2-butylene glycol, 2,3-butylene glycol, styrene glycol, diethylene glycol, triethylene glycol, tetraethylene glycol and other poly (ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co.

Therefore the present invention also relates to a hot-melt extruded formulation (HEF$^8$), which is (HEF), (HEF$^1$), (HEF$^2$), (HEF$^3$), (HEF$^4$), (HEF$^5$), (HEF$^8$) or (HEF$^7$), wherein the hot-melt extruded formulation additionally comprises at least one plasticizer chosen form the group consisting of ethylene glycol, 1,2-butylene glycol, 2,3-butylene glycol, styrene glycol, diethylene glycol, triethylene glycol, tetraethylene glycol and other poly (ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate.

The amount of plasticizer used in the hot-melt extruded formulation will depend upon its composition, physical properties, effect upon the hot-melt extrusion formulation, interaction with other components of the hot-melt extrusion formulation and other such reasons. Generally, the plasticizer content will not exceed about 40 wt-%, based on the total weight of the hot-melt extruded formulation.

Therefore the present invention also relates to a hot-melt extruded formulation (HEF$^9$), which is (HEF), (HEF$^1$), (HEF$^2$), (HEF$^3$), (HEF$^4$), (HEF$^5$), (HEF$^6$), (HEF$^7$) or (HEF$^8$), wherein the hot-melt extruded formulation comprises 10-40 wt-%, based on the total weight of the hot-melt extruded formulation, of at least one plasticizer Furthermore the hot melt extruded formulation can comprise other ingredients, such as for example, dyes, flavours, binders, fillers, lubricants, flow agents etc. The use of such compounds are usually needed (or desired) to improve the property of the final end-market product (food, feed and dietary supplement products).

A further ingredient class which can be used in a hot-melt extruded formulation are antioxidants.

As used herein, the term "antioxidant" is intended to mean an agent that inhibits oxidation and thus is used to prevent the deterioration of preparations by oxidation due to the presence of oxygen free radicals or free metals in the composition. Such compounds include, by way of example and without limitation, ascorbic acid, ascorbyl palmitate, butylated hydroxyanisole, butylated hydroxytoluene, hypophophorous acid, monothioglycerol, sodium ascorbate, sodium formaldehyde sulfoxylate, sodium metabisulfite, sodium metabisulfite (or other sulfite derivatives), BHT, BHA, vitamin E and its derivatives or propyl gallate, and others known to those of ordinary skill in the art.

Therefore the present invention also relates to a hot-melt extruded formulation ($HEF^{10}$), which is (HEF), ($HEF^1$), ($HEF^2$), ($HEF^3$), ($HEF^4$), ($HEF^5$), ($HEF^6$), ($HEF^7$), ($HEF^8$) or ($HEF^9$), wherein the hot-melt extruded formulation additionally comprises at least one antioxidant.

Therefore the present invention also relates to a hot-melt extruded formulation ($HEF^{11}$), which is (HEF), ($HEF^1$), ($HEF^2$), ($HEF^3$), ($HEF^4$), ($HEF^5$), ($HEF^6$), ($HEF^7$), ($HEF^8$), ($HEF^9$) or ($HEF^{10}$), wherein the hot-melt extruded formulation additionally comprises at least one antioxidant chosen from the group consisting of ascorbic acid, ascorbyl palmitate, butylated hydroxyanisole, butylated hydroxytoluene, hypophophorous acid, monothioglycerol, sodium ascorbate, sodium formaldehyde sulfoxylate, sodium metabisulfite, sodium bisulfite (or other sulfite derivatives), BHT, BHA, vitamin E and its derivatives, and propyl gallate.

The amount is usually not higher than 5 wt-%, based on the total weight of the hot-melt extruded formulation.

Therefore the present invention also relates to a hot-melt extruded formulation ($HEF^{12}$), which is (HEF), ($HEF^1$), ($HEF^2$), ($HEF^3$), ($HEF^4$), ($HEF^5$), ($HEF^6$), ($HEF^7$), ($HEF^8$), ($HEF^9$), ($HEF^{10}$) or ($HEF^{11}$), wherein the hot-melt extruded formulation comprises up to 5 wt-%, based on the total weight of the hot-melt extruded formulation, of at least one antioxidant.

Pharmaceutical formulations comprised of active compounds finely and homogenously dispersed in one or more polymeric carriers have been described as solid dispersions, glass solutions, molecular dispersions, and solid solutions. The same applies for the compounds as used in the present holt-met extruded formulation. The term solid dispersion has been used as a general term to describe pharmaceutical preparations in which the active compound is dispersed in an inert excipient carrier in a size range from coarse to fine. Glass solution, molecular dispersion, and solid solution refer specifically to preparations in which amorphous forms of a crystalline active compound are formed in-situ and dispersed within the polymer matrix during the hot-melt extrusion process.

The formulation according to the present invention is produced by a hot-melt extrusion method. All preferences as described above are obviously also valid for the production of these formulations.

Therefore the present invention relates to a hot-melt extrusion process (HEP) for the production of a hot melt extruded formulation, wherein
  (i) 0.5-50 weight-% (wt-%), preferably 5-20 wt-%, more preferably 5-10 wt-%, based on the total weight of the hot-melt extruded formulation, of at least one compound having low permeability and low solubility, and
  (ii) 50-99.5 wt-%, preferably 80-95 wt-%, more preferably 90-95 wt-%, based on the total weight of the hot-melt extruded formulation, of at least one polymeric carrier material,
in the absence of any solvent are hot-melt extruded.

All the above described hot-melt extruded formulations (HEF), ($HEF^1$), ($HEF^2$), ($HEF^3$), ($HEF^4$), ($HEF^5$), ($HEF^6$), ($HEF^7$), ($HEF^8$), ($HEF^9$), ($HEF^{10}$), ($HEF^{11}$) and ($HEF^{12}$), are produced by the process (HEP).

Hot-melt extrusion processes are known from the prior art.

The term "hot-melt extrusion" is used herein to describe a process whereby an excipient blend is heated to a molten state and subsequently forced through an orifice where the extruded product is formed into its final shape in which it is solidified upon cooling. The blend is conveyed through various heating zones typically by a screw mechanism. The screw or screws are rotated by a variable speed motor inside a cylindrical barrel where only a small gap exists between the outside diameter of the screw and the inside diameter of the barrel. In this conformation, high shear is created at the barrel wall and between the screw fights by which the various components of the powder blend are well mixed and deaggregated. The hot-melt extrusion equipment is typically a single or twin-screw apparatus, but can be composed of more than two screw elements. A typical hot-melt extrusion apparatus contains a mixing/conveying zone, a heating/melting zone, and a pumping zone in succession up to the orifice. In the mixing/conveying zone, the powder blends are mixed and aggregates are reduced to primary particles by the shear force between the screw elements and the barrel. In the heating/melting zone, the temperature is at or above the melting point or glass transition temperature of the polymeric carrier in the blend such that the conveying solids become molten as they pass through the zone. The polymeric carrier acts as the matrix in which the active or actives and other functional ingredients are dispersed, or the adhesive with which they are bound such that a continuous composite is formed at the outlet orifice. Once in a molten state, the homogenized blend is pumped to the orifice through another heating zone that maintains the molten state of the blend. At the orifice, the molten blend can be formed into strands, cylinders or films. The extrudate that exits is then solidified typically by an air-cooling process. Once solidified, the extrudate may then be further processed to form pellets, spheres, fine powder, tablets, and the like.

An example of a single screw apparatus similar to the description above is the Randcastle Microtruder, model RCP-0750.

Examples for twin-screw aparati are Xplore 5 cc conical or Thermo Scientific Haake Polylab OS Rheodrive7, Haake Rheomex OS PTW 16.

Temperature is an important process variable to consider for the proposed invention.

The hot-melt extrusion process preferably employed is conducted at an elevated temperature, i. e. the heating zone(s) of the extruder is above room temperature (about 20° C.). It is important to select an operating temperature range that will minimize the degradation or decomposition of the compounds during processing. The operating temperature range is generally in the range of from about 50° C. to about 300° C. as determined by the setting for the extruder heating zone(s). The temperature of the mixture being hot-melt extruded will not exceed 300° C. and preferably will not exceed 250° C.

Therefore the present invention also relates to a hot-melt extrusion process ($HEP^1$), which is (HEP), wherein the operating temperature range is generally in the range of from about 50° C. to about 300° C. for the extruder heating zone(s), preferably the temperature of the mixture being hot-melt extruded will not exceed 300° C. and more preferably will not exceed 250° C.

All ingredients used are in a dry state (no solvent!), are placed into a mixer or hopper and agitated (blended) until thoroughly mixed. This mixture is then hot-melt extruded at a rate and temperature sufficient to melt or soften the polymeric carrier material, to minimize degradation of the components and to form an extrudate which is subsequently ground or chopped into suitable particles.

Consideration should be given to the manner in which the components of a formulation are fed to the extruder. In some embodiment, all formulation components are blended together to form a blended mixture before being fed to the extruder. This can be done by any traditional mixing or blending technique. Alternatively, formulation components may be fed individually if done simultaneously, and given that there is adequate mixing of the formulation components in the mixing/conveying zone of the extruder.

Usually and preferably no solvent is used in the hot-melt extrusion.

The extruder used to practice the invention can be any such commercially available model equipped to handle dry feed and having a solid conveying zone, one or multiple heating zones, and an extrusion die. A two stage single screw extruder, such as that manufactured by BRABENDER or KILLION are two such apparati. It can be advantageous for the extruder to possess multiple separate temperature controllable heating zones.

Many conditions can be varied during the extrusion process to arrive at a particularly advantageous formulation. Such conditions include, by way of example, formulation composition, feed rate, operating temperature, extruder screw RPM, residence time, die configuration, heating zone length and extruder torque and/or pressure. Methods for the optimization of such conditions are known to a person skilled in the art.

By including a plasticizer, and, optionally, an antioxidant, in a formulation, processing temperature, pressure and/or torque may be reduced. Plasticizers (as well as antioxidants) are not required in order to practice the invention. Their addition to the formulation is contemplated as being within the scope of the invention.

The hot-melt extruded formulations (HEF), (HEF$^1$), (HEF$^2$), (HEF$^3$), (HEF$^4$), (HEF$^5$), (HEF$^6$), (HEF$^7$), (HEF$^8$), (HEF$^9$), (HEF$^{10}$), (HEF$^{11}$) and (HEF$^{12}$) as described above can be used as or in a food product, feed product and/or dietary supplement.

It is also possible to use such formulation is premixes, which are then used to formulate the final end-product.

Therefore the present invention also relates to the use of at least one hot-melt extruded formulation (HEF), (HEF$^1$), (HEF$^2$), (HEF$^3$), (HEF$^4$), (HEF$^5$), (HEF$^6$), (HEF$^7$), (HEF$^8$), (HEF$^9$), (HEF$^{10}$), (HEF$^{11}$) and/or (HEF$^{12}$) in a food product, feed product and/or dietary supplement.

Therefore the present invention also relates to the use of hot-melt extruded formulations as described and disclosed above in a premix for a food product, feed product and/or dietary supplement.

Therefore the present invention also relates a food product, feed product and/or dietary supplement comprising at least one hot-melt extruded formulation (HEF), (HEF$^1$), (HEF$^2$), (HEF$^3$), (HEF$^4$), (HEF$^5$), (HEF$^6$), (HEF$^7$), (HEF$^8$), (HEF$^9$), (HEF$^{10}$), (HEF$^{11}$) or (HEF$^{12}$).

Therefore the present invention also relates a premix for a food product, feed product and/or dietary supplement comprising at least one hot-melt extruded formulation (HEF), (HEF$^1$), (HEF$^2$), (HEF$^3$), (HEF$^4$), (HEF$^5$), (HEF$^6$), (HEF$^7$), (HEF$^8$), (HEF$^9$), (HEF$^{10}$), (HEF$^{11}$) or (HEF$^{12}$).

The invention is illustrated by the following Examples. All temperatures are given in ° C. and all parts and percentages are related to the weight.

EXAMPLES

Example 1

The hot-melt extrusion (HME) process of β-carotene was performed with a Xplore 5 cc conical, co-rotating, twin-screw microcompounder. Hydroxypropyl methylcellulose (HPMC; Methocel E5 or Methocel E19 from Dow Chemicals), polyethylene glycol (PEG 200 from Sigma Aldrich) and crystalline β-carotene (DSM Nutritional Products Ltd.) were manually premixed at a ratio 59.4/39.6/1 wt %, respectively. The premix was fed with a horizontal piston into the extruder that was purged with nitrogen. The temperature of all barrels was set to 160° C. An initial screw speed of 250 rpm was selected for 2 minutes followed by 400 rpm for 8 minutes. The extrudate was then collected by opening the valve at the bottom of the extruder at a reduced screw speed of 150 rpm. The extrudates were dissolved in water and the β-carotene dispersion size was determined by laser diffraction (Malvern Instruments Mastersizer 3000). The resulting dispersion size distribution was monomodal with mean sizes $d_{10}=0.457$ μm, $d_{50}=0.637$ μm and $d_{90}=0.901$ μm.

Example 2

The hot-melt extrusion (HME) process of β-carotene was performed with a Xplore 5 cc conical, co-rotating, twin-screw microcompounder. A polyvinylcaprolactam—polyvinyl acetate—polyethylene glycol graft co-polymer (Soluplus from BASF) and crystalline β-carotene (DSM Nutritional Products Ltd.) were manually premixed. The β-carotene content was 1 wt %. The premix was fed with a horizontal piston into the extruder that was purged with nitrogen. The temperature of all barrels was set to 160° C. A screw speed of 250 rpm was selected and mixing was performed during 5 minutes. The screw speed was then reduced to 50 rpm and the mixture was extruded through the bottom opening by turning the valve. The extruded strand was let cool down to room temperature. The extrudates were dissolved in water and the β-carotene dispersion size was measured by photocorrelation spectroscopy (Beckman Coulter Delsa Nano S Particle Analyzer). Fine, monomodal distributions were obtained with mean sizes $d_{10}=43.9$ nm, $d_{50}=62.8$ nm and $d_{90}=91.1$ nm. The dispersion size in an extrudate with 2 wt % β-carotene was similar with $d_{10}=50.1$ nm, $d_{50}=57.5$ nm and $d_{90}=66.1$ nm. The crystallinity of β-carotene before and after HME was measured by differential scanning calorimetry (DSC). The samples were weighted in 50 μL sealed aluminum pans with a hole in the lid and heated from 20 to 195° C. at 5° C./min. Pure crystalline β-carotene had a DSC melting peak at ~182° C. The β-carotene melting peak was no longer visible after HME indicating the loss of crystallinity by HME.

Example 3

Continuous hot-melt extrusion (HME) of β-carotene was performed on a co-rotating, twin-screw extruder (Thermo Scientific Haake Polylab OS Rheodrive7, Haake Rheomex OS PTW 16). A premix of β-carotene and HPMC (Methocel E19 from Dow Chemicals) was prepared by blending the sieved powders for 20 minutes under nitrogen. The premix was added to the first barrel of the extruder with a gravimetric feeder (Brabender Technologie) at 502 g/h. PEG 200 (Sigma Aldrich) was fed with a liquid pump (HNP Mikrosystem) at 329 g/h to the next downstream barrel. The composition of the extrudate was thus 59.4/39.6/1 wt % HPMC, PEG 200 and β-carotene, respectively. All barrels were heated to 160° C. and a screw speed of 450 rpm was selected. A die with a diameter of 1 mm was mounted on the extruder head and the extrudate strand was cooled down to room temperature on a conveyor belt. The β-carotene dispersion size was determined by laser diffraction as described in Example 1. A monomodal size distribution was obtained with mean sizes $d_{10}=0.407$ μm, $d_{50}=0.548$ μm and $d_{90}=0.734$ μm. The crystallinity of β-carotene before and after continuous HME was measured by DSC as described in Example 2. The endothermic melting peak of β-carotene was not detected in DSC curves of the extrudates.

The invention claimed is:

1. A hot-melt extruded formulation comprising:
   (i) 0.5-50 wt-%, based on the total weight of the hot melt extruded formulation, of at least one compound having low permeability and low solubility selected from the group consisting of α-carotene, β-carotene, 8'-apo-β-carotenal, 8'-apo-β-carotenoic acid esters, canthaxanthin, astaxanthin, lycopene, lutein, zeaxanthin and crocetin,
   (ii) 50-99.5 wt-%, based on the total weight of the hot melt extruded formulation, of at least one polymeric carrier material selected from the group consisting of ethyl cellulose (EC), hydroxypropylmethyl cellulose (HPMC), alginate, chitosan, corn starch, potato starch, polyvinylpyrrolidon (PVP), polyvinylacetate (PVA), polylactic acid (PLA), poly(methacrylic acid-co-ethyl acrylate) and polyvinyl caprolactam-polyvinyl acetate-polyethylene glycol graft copolymer, and
   (iii) up to about 40 wt-%, based on the total weight of the hot melt extruded formulation, of at least one plasticizer selected from the group consisting of ethylene glycol, 1,2-butylene glycol, 2,3-butylene glycol, styrene glycol, diethylene glycol, triethylene glycol, tetraethylene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate.

2. The hot-melt extruded formulation according to claim 1, wherein the compound having low permeability and low solubility is in an amorphous form.

3. The hot-melt extruded formulation according to claim 1, wherein the at least one plasticizer is present in an amount of 10-40 wt-%, based on the total weight of the hot-melt extruded formulation.

4. The hot-melt extruded formulation according to claim 1, further comprising at least one antioxidant.

5. The hot-melt extruded formulation according to claim 4, wherein the at least one antioxidant is selected from the group consisting of ascorbic acid, ascorbyl palmitate, butylated hydroxyanisole, butylated hydroxytoluene, hypophosphorous acid, monothioglycerol, sodium ascorbate, sodium formaldehyde sulfoxylate, sodium metabisulfite, vitamin C, BHT, BHA, sodium bisulfite, vitamin E and derivatives thereof, and propyl gallate.

6. The hot-melt extruded formulation according to claim 4, wherein the at least one antioxidant is present in an amount up to 5 wt-%, based on the total weight of the hot-melt extruded formulation.

7. The hot-melt extruded formulation according to claim 1, wherein the formulation comprises:
   (i) 5-20 wt-%, based on the total weight of the hot melt extruded formulation, of the at least one compound having low permeability and low solubility,
   (ii) 80-95 wt-%, based on the total weight of the hot melt extruded formulation, of the at least one polymeric carrier material, and
   (iii) 10-40 wt-%, based on the total weight of the hot melt extruded formulation, of the at least one plasticizer.

8. The hot-melt extruded formulation according to claim 1, wherein the formulation comprises:
   (i) 5-10 wt-%, based on the total weight of the hot melt extruded formulation, of the at least one compound having low permeability and low solubility,
   (ii) 90-95 wt-%, based on the total weight of the hot melt extruded formulation, of the at least one polymeric carrier material, and
   (iii) 10-40 wt-%, based on the total weight of the hot melt extruded formulation, of the at least one plasticizer.

9. A food product, feed product and/or dietary supplement comprising the hot-melt extruded formulation according to claim 1.

10. A premix for a food product, feed product and/or dietary supplement comprising the hot-melt extruded formulation according to claim 1.

11. A hot-melt extrusion process for the production of a hot melt extruded formulation, wherein the process comprising conducting hot-melt extrusion in the absence of a solvent of formulation components comprising:
    (i) 0.5-50 weight-% (wt-%), based on the total weight of the hot-melt extruded formulation, of at least one compound having low solubility selected from the group consisting of α-carotene, β-carotene, 8'-apo-β-carotenal, 8'-apo-β-carotenoic acid esters, canthaxanthin, astaxanthin, lycopene, lutein, zeaxanthin and crocetin,
    (ii) 50-99.5 wt-%, based on the total weight of the hot-melt extruded formulation, of at least one polymeric carrier material selected from the group consisting of ethyl cellulose (EC), hydroxypropylmethyl cellulose (HPMC), alginate, chitosan, corn starch, potato starch, polyvinylpyrrolidon (PVP), polyvinylacetate (PVA), polylactic acid (PLA), poly(methacrylic acid-co-ethyl acrylate) and polyvinyl caprolactam-polyvinyl acetate-polyethylene glycol graft copolymer, and
    (iii) up to about 40 wt-%, based on the total weight of the hot melt extruded formulation, of at least one plasticizer selected from the group consisting of ethylene glycol, 1,2-butylene glycol, 2,3-butylene glycol, styrene glycol, diethylene glycol, triethylene glycol, tetraethylene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate.

12. The hot-melt extrusion process according to claim 11, which comprises conducting hot-melt extrusion of 5-20 wt-% of component (i), 80-95 wt-% of component (ii) and 10-40 wt-% of component (iii).

13. The hot-melt extrusion process according to claim 11, which comprises conducting hot-melt extrusion of 5-10 wt-% or component (i), 90-95 wt-% of component (ii) and 10-40 wt-% of component (iii).

* * * * *